United States Patent [19]
Kittur et al.

[11] Patent Number: 5,846,241
[45] Date of Patent: Dec. 8, 1998

[54] BIPOLAR ELECTROCAUTERY VALVULOTOME

[75] Inventors: Dilip Kittur, Baltimore; John Petronis, Perry Hall, both of Md.

[73] Assignee: Johns Hopkins University, Baltimore, Md.

[21] Appl. No.: 768,620

[22] Filed: Dec. 18, 1996

Related U.S. Application Data

[60] Provisional application No. 60/008,876 Dec. 19, 1995.

[51] Int. Cl.⁶ .................................................. A61B 17/39
[52] U.S. Cl. .............................................. 606/48; 606/50
[58] Field of Search ................................. 606/41, 45, 46, 606/48, 50

[56] References Cited

U.S. PATENT DOCUMENTS

| | | |
|---|---|---|
| 3,837,345 | 9/1974 | Matar . |
| 4,924,882 | 5/1990 | Donovan .................................... 606/45 |
| 5,026,383 | 6/1991 | Nobles . |
| 5,047,041 | 9/1991 | Samuels . |
| 5,069,679 | 12/1991 | Taheri . |
| 5,085,659 | 2/1992 | Rydell ......................................... 606/48 |
| 5,125,928 | 6/1992 | Parins et al. ............................... 606/48 |
| 5,190,541 | 3/1993 | Abele et al. ............................... 606/48 |
| 5,197,964 | 3/1993 | Parins ......................................... 606/48 |
| 5,234,450 | 8/1993 | Segalowitz . |
| 5,284,478 | 2/1994 | Nobles . |
| 5,304,189 | 4/1994 | Goldberg . |

*Primary Examiner*—Lee Cohen
*Attorney, Agent, or Firm*—Pillsbury Madison & Sutro, LLP; Intellectual Property Group of Pillsbury Madison & Sutro, LLP

[57] ABSTRACT

A bipolar electrocautery valvulotome in the form of an elongated catheter having a longitudinal axis, a proximal end for being held and manipulated by a user, and a distal end. A first electrode is provided adjacent the distal end of a main body of the catheter and has an exposed surface facing distally of the catheter. The first electrode is electrically coupled to device for generating a current. A second electrode is disposed distally of the first electrode and is also electrically coupled to the current generating device. The second electrode has an exposed surface in a plane substantially perpendicular to the longitudinal axis of the catheter. At least one of the first and second electrodes is movable relative to the other so as to selectively capture a venous valve structure to be cauterized therebetween.

18 Claims, 3 Drawing Sheets

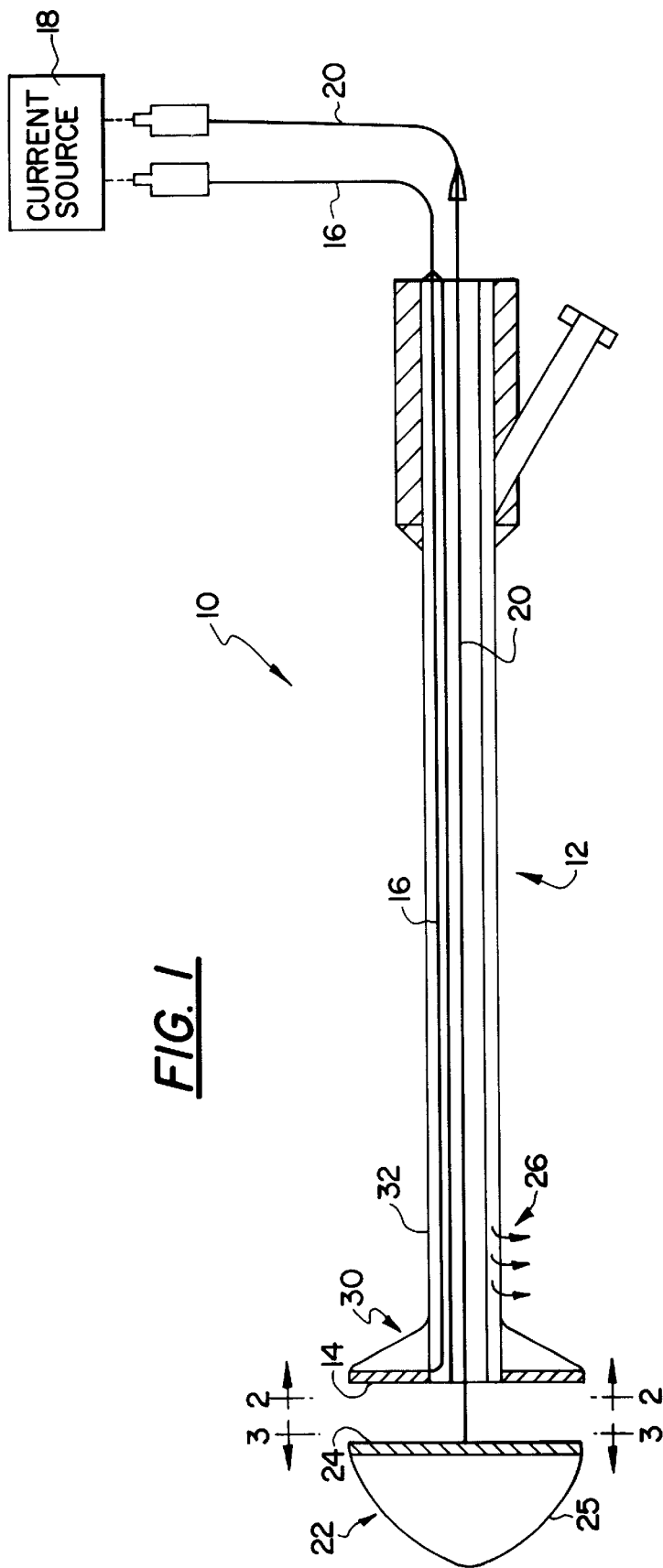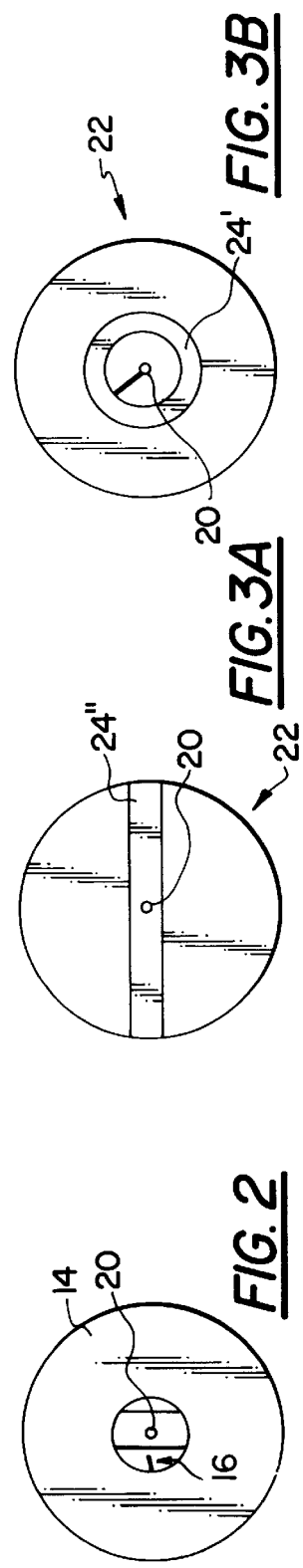

BIPOLAR ELECTROCAUTERY VALVULOTOME

This application claims the benefit of U.S. Provisional Appln. No. 60/008,876, filed Dec. 19, 1995.

BACKGROUND OF THE INVENTION

1. Field of the Invention

The present invention relates to apparatuses for removing or disabling valves within veins and more particularly to an electrocautery valvulotome. The invention also relates to side-branch ligation in conjunction with bypass graft procedures.

2. Description of Related Art

There are several surgical procedures of which cutting valves in veins is an integral part. Exemplary procedures include bypass grafts in lower extremities and coronary artery bypass grafts. Several mechanical valvulotomes have been devised to date to cut valves in veins.

The most common valvulotome in use is the mechanical valvulotome, of which Leather & Karmody is an example, which is a set of instruments consisting of knives and scissors specially designed to be passed into veins to cut the valves mechanically.

A disadvantage with the conventional valvulotome, exemplified by the Leather & Karmody valvulotome, is that there is a considerable learning curve, and its use is time consuming even for the experienced surgeon. Another disadvantage of the mechanical valvulotome is that multiple incisions in the vein have to be made to pass the valvulotome. Yet another disadvantage of the mechanical valvulotome is the possibility of injury to the walls of the vein. Moreover, there is the possibility that a valve could be missed since the valvulotome could slip past the valve. This potential problem is of major concern as it would lead to intraoperative angiograms and increased length of the primary surgical procedure.

Yet a further perceived disadvantage with the mechanical valvulotome is that it is designed to make a radial cut in the valve rather than a circular cut, which would excise the valve completely. Some recently developed valvulotome designs have addressed this issue and proposed to cut the valve in a circular fashion. Nevertheless, the other disadvantages noted above remain.

Other known valvulotomes are not in very frequent use at the present time but most have one or more of the problems discussed above with respect to the mechanical valvulotome.

SUMMARY OF THE INVENTION

It is an object of this invention to provide a valvulotome that can be quickly and effectively used to disable venous valves via a single incision.

It is likewise an object of the invention to provide a valvulotome which minimizes trauma to the side walls of the vein.

It is also an object of the invention to provide a valvulotome wherein the valve disabling action is adjustable and therefore more control can be exercised on the excision of the valve.

It is a further object of the present invention to provide a valvulotome that may be adapted to cut venous valves in a circular or circumferential manner and therefore overcome the potential disadvantages of incising but not removing valves completely.

The foregoing and other objects of the invention are realized by providing a valvulotome including first and second opposed electrodes, one mounted for movement relative to the other. In use a valve to be disabled is located between the electrodes and the electrode(s) are displaced into engagement with the valve leaflets. An electrical current source coupled to the electrodes is then actuated whereby the valve is ablated.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 1 is a schematic cross-section of an electrocautery valvulotome provided in accordance with the present invention;

FIG. 2 is an end view of an exemplary fixed electrode configuration provided in accordance with the present invention, taken along line 2—2 of FIG. 1;

FIG. 3A is a first alternate embodiment of a moveable electrode configuration in accordance with the invention, taken along line 3—3 of FIG. 1;

FIG. 3B is a second alternate moveable electrode configuration in accordance with the invention, taken along line 3—3 of FIG. 1;

DETAILED DESCRIPTION OF THE PRESENTLY PREFERRED EXEMPLARY EMBODIMENTS

Figure 4A:
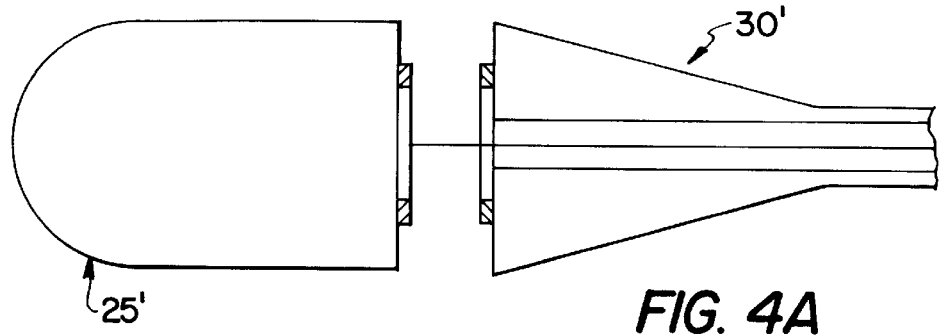
FIGS. 4A and 4B illustrate exemplary alternate configurations of the moveable head and fixed electrode components of the valvulotome provided in accordance with the present invention.

With reference to FIG. 1, the electrocautery device 10 provided in accordance with the present invention includes, by way of example, a multiple lumen catheter 12 having a fixed electrode 14 exposed at the distal end of the catheter main body. In the embodiment illustrated in FIG. 1, the fixed electrode 14 is generally circular in plan view (FIG. 2). A flexible wire 16 is electrically coupled to the fixed electrode 14 and operatively coupled to an adjustable bipolar or multipolar cautery current source 18 which may be of any suitable construction available. A second wire 20 extends through one of the lumens of the catheter 12 and is electrically coupled to a moveable head 22 having a second electrode 24 defined on a face thereof, in opposition to the fixed electrode 14. The terms "fixed" and "movable" as used herein are for convenience and should be understood to be relative terms. Thus, the "fixed" electrode can be moved relative to the "movable" electrode while the latter is held in a fixed disposition and vice versa, or both electrodes can be moved at the same time.

By way of example, the valvulotome of the invention may be used as a part of an in situ saphenous vein bypass procedure. In use, the entire catheter assembly 10 including moveable head 22 and wire 20 coupled thereto is inserted into the vein through a venotomy incision at the distal end of the vein segment of interest. The catheter with electrodes abutting is advanced to the proximal end of the vein, remote from the venotomy incision.

In accordance with the invention, the distal or forward end of the movable head is generally convexly curved as at 25, 25', 25", for example bullet shaped, so that it can be advanced through the venous valve(s) in the direction of normal blood flow. That the distal end has reached the end of the vein or vein segment, may be confirmed by injecting dye through port(s) 26 of the catheter 12 and examining an image of the vein or vein segment.

The moveable head 22 then is pushed away from the fixed electrode 14 or the fixed electrode 14 is retracted to suitably space the electrodes, as appropriate to the procedure and the valvulotome structure being utilized. Of course for the movable head 22 to be advanced relative to the fixed electrode, the flexible coated guide wire 20 extending proximally therefrom (FIG. 1) must be sufficiently rigid for controlled advancement, otherwise retraction of the fixed electrode would be preferred. In the event a conduit 28 extends proximally from the movable head, as in the embodiment of FIGS. 6A and B, moveable head advancement independently of the fixed electrode 14 is clearly an option.

Figure 4B:
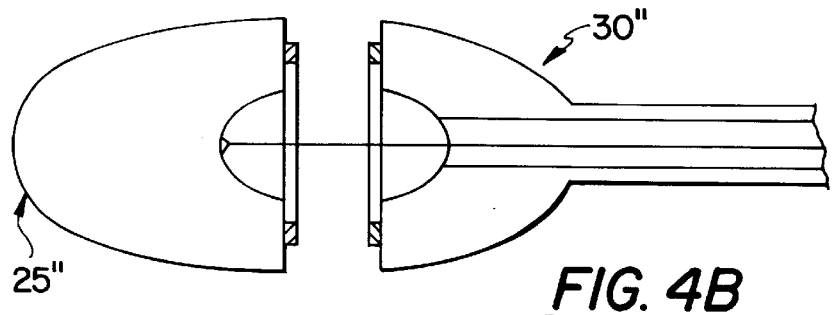

Once the movable head 22 and fixed electrode 14 are suitably spaced, the fixed electrode is retracted independently or simultaneously with the movable head so that the fixed electrode 14 passes through the valve. Providing a fixed electrode having an arcuate proximal surface as at 30, 30', 30" defining a gradual transition from the catheter body 32 will facilitate passage of the fixed electrode back through the valve, as is apparent from FIGS. 1, 4A and 4B.

Figure 5A:
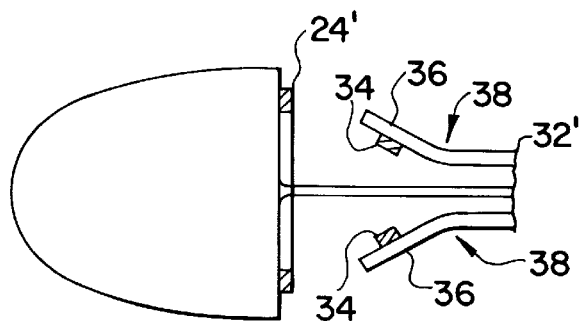
FIGS. 5A and 5B illustrate another exemplary embodiment of the valvulotome head with electrodes, in non-engaged and engaged dispositions, respectively.
Figure 5B:
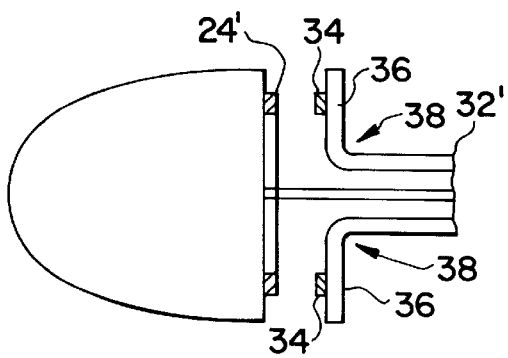

As an alternative to providing an arcuate proximal surface 30 for the fixed electrode, the so-called fixed electrode 14 may be provided as electrode segments 34 on each of two or more flexing tabs or wings 36 defined at the distal end of the catheter. Where a plurality of electrode segments 34 are provided each must be suitably electrically coupled to the cautery device 18 as will be apparent to one skilled in the art. Such tabs or wings 36 extend via a living hinge or the like 38 from the main body 32' of the catheter. Isolated tabs or wings permit the distal end of the catheter structure to which the fixed electrodes are coupled to collapse for ease of passage back through the venous valve. The tabs are preferably configured so as to project at an angle from the longitudinal axis of the catheter when not exposed to a collapsing or spreading force as shown in FIG. 5A. Such an inclined structure facilitates passage of the catheter back through the valve but ensures that, on advancement of the catheter towards the movable head as explained in greater detail below, the electrode segment carrying tabs or wings 36 can be deflected to a substantially orthogonal disposition as shown in FIG. 5B. In that disposition the fixed electrode segment(s) 34 will be in opposed facing relation to the electrode(s) 24' of the movable head. As can be appreciated, where tabs or wings are provided for carrying electrodes, their number and configuration can be varied greatly without departing from the principles of the invention, provided they are of sufficient size and dimensions so as to be deflected to the disposition shown in FIG. 5B upon engagement with a venous valve and not buckle or collapse when exposed to such an axial force; and so as to present an electrode surface of sufficient size and in an appropriate orientation to effectively disable a valve upon actuation.

Returning again to the use of the inventive valvulotome, once the fixed electrode has passed through the valve, the valve will collapse or close against the coated wire intermediate the fixed and movable electrodes. Upon further withdrawal of the catheter, the flat face of the movable head will engage the valve. Hence, further displacement will be resisted. When such resistance is detected, with the coated guide wire held steady, the catheter main body with the fixed electrode at its distal end is pushed toward the moveable head. This motion will capture the valve between the two electrodes.

A bipolar electrical current is then applied to initiate cautery action. A gentle force is kept on the valvulotome while the current is applied to ablate the valve. Pulling back on the moveable head will indicate whether the valve has been completely ablated. Following completion of the cautery procedure, the moveable head is disengaged from the fixed electrode.

Once the moveable head has been disengaged from the fixed electrode following ablation of the valve, the catheter is withdrawn in an open position to engage the next valve. In order to evaluate the success of the valve excision, dye may be injected through the catheter port(s) 26 to access the valve and venous anatomy.

As is apparent from the foregoing, providing electrodes 24, 24' having a generally circular configuration (FIGS. 1, 3B) will effect a circular ablation of the valve structure. Providing electrodes of other configurations (e.g. as electrode 24" shown in FIG. 3A) will disable the valves in other ways such as by radial ablation or part circular ablation.

As can be appreciated, the fixed and moveable electrodes may be provided in any one of several sizes and configurations so as to allow passage through the valves in the direction of (venous) blood flow and then selective retraction through the vein to allow excision of the valve structures. It is to be noted in this regard that the catheter of the invention may advantageously be provided with interchangeable guide wire and moveable head assemblies or otherwise detachable and interchangeable fixed and/or moveable electrode components or heads to accommodate the surgical procedure, the patient's physiology or the "cut" or ablation pattern desired. One skilled in this art upon a review of this disclosure would appreciate how such modifications could be effected. By way of example, a variety of moveable and fixed electrode heads are illustrated, but not deemed to be limiting.

Figure 6A:
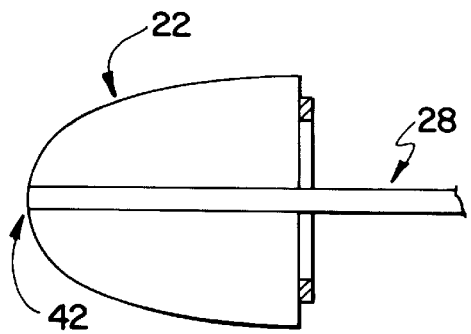
FIGS. 6A and 6B illustrate further exemplary alternate embodiments of the valvulotome of the present invention wherein the moveable head has a passage defined therethrough.
Figure 6B:
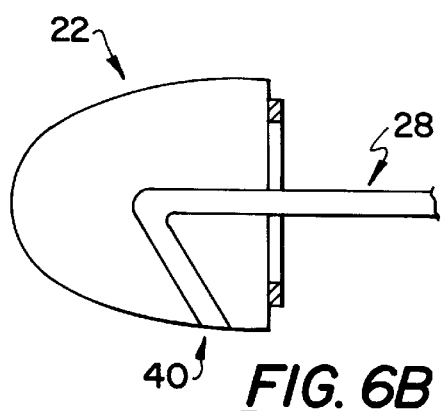
Figure 7:
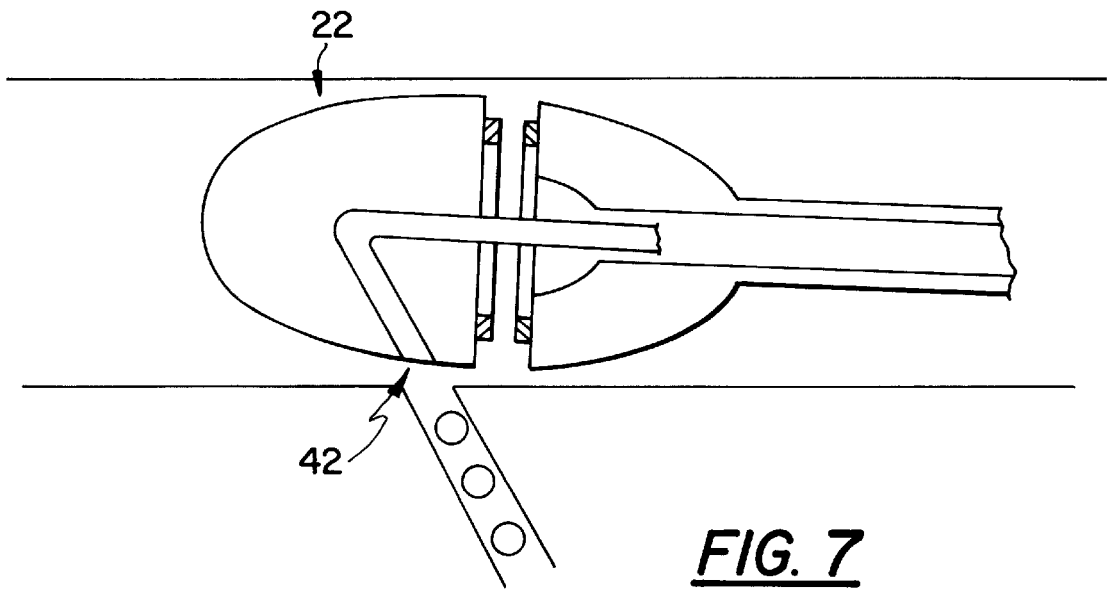
FIG. 7 illustrates an exemplary use of the valvulotome of FIG. 6B.
Figure 8:
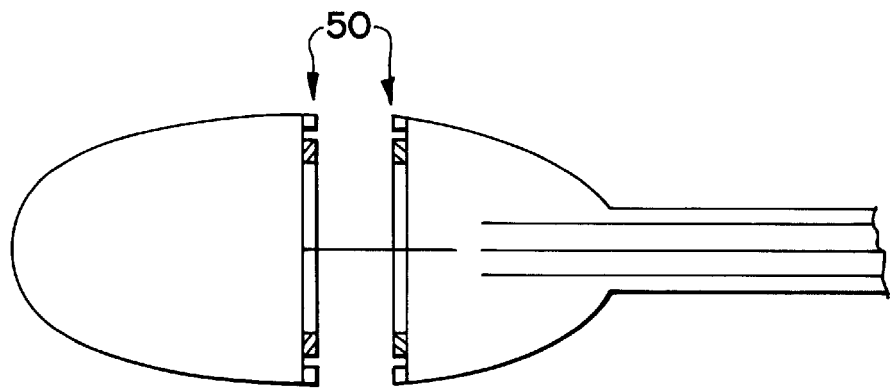
FIG. 8 illustrates a further optional feature of the invention.

With reference to FIGS. 6A and 6B, it can be seen that in accordance with the invention, the moveable head 22 may be coupled to a longitudinally extending conduit 28 to permit the infusion of fluids at, as at 40, or beyond, as at 42, the moveable head. For example, as shown in FIG. 7, a structure of the type shown in FIG. 6B may be used to inject suitable material, such as a gel foam, to close off a branch vessel, a procedure known as branch ligation. As an alternative to injecting such material(s) through conduit 28, another, flexible tube may be inserted through conduit 28, through which suitable material(s) may be injected. The advantages of such a separate tube, including greater versatility and procedural options will be readily apparent to one skilled in the art.

The provision of an infusion conduit as in FIGS. 6A and B, furthermore, facilitates a determination of the position of the moveable electrode relative to the fixed electrode by observation of the relative position of the proximal end of the catheter main body relative to the proximal end of the conduit, when the valvulotome is disposed within the target vein. Moreover, it is contemplated that the handle structure of the valvulotome will allow the operator to sense resistance of the valve and to determine through tactile feel feedback the relative position and disposition of the components of the structure.

In accordance with a further feature of the invention, an insulating lip 50, is provided in surrounding relation or adjacent to one or both electrode(s) provided on the respective heads to protect the vein surface from discharge through the electrodes. The lip may be separately provided, for example made of an insulating, bio-compatible, resilient material and secured to the head(s) or integrally formed therewith. In accordance with a further feature of the invention, it is contemplated that triggering of current will only be enabled when the electrodes are closely adjacent and/or both closely touching the target valve to minimize the potential for a spark jumping the gap between electrodes, which may risk damage to the vein wall. For example, when the insulating lip is provided, current may only be enabled when the lip(s) are in contact with the valve structure.

In another procedure in which the invention could be used, a vein is grafted or anastomosed in situ to an artery. The vein is pressurized by arterial blood flow to the vein, thereby causing the first valve leaflet pair to close tightly. The valvulotome is inserted from the distal end into the proximal most portion of the vein, near the grafting site. The catheter is then drawn down through the vein such that the fixed electrode passes through the valve leaflets so that the valve is disposed between the moveable head and the fixed electrode. Because of its shape, passage of the moveable head, through the valve leaflets is resisted. The fixed electrode is then advanced towards the moveable head to sandwich the valve leaflet pairs between the electrodes and the current source is actuated.

Following ablation of the leaflet pair, the next adjacent segment of the vein will be pressurized with blood and the moveable head can easily move with the fixed electrode through the vein approaching the next leaflet pair with minimal trauma to the vein walls. Again the fixed electrode is displaced from the moveable head to pass through the leaflet pair. The moveable head is advanced to the leaflet pair and into engagement therewith. Finally, the fixed electrode is advanced towards the moveable head to sandwich the leaflet pair between opposing electrodes. In this manner the leaflets in the vein can be sequentially rendered incompetent quickly and reliably.

While the invention has been described in connection with what are presently considered to be the most practical and preferred embodiments, it is to be understood that the invention is not to be limited to the disclosed embodiments, but on the contrary is intended to cover various modifications and equivalent arrangements included within the spirit and scope of the appended claims.

We claim:

1. A bipolar electrocautery valvulotome comprising:
    an elongated catheter main body having a longitudinal axis, a proximal end for being held and manipulated by a user, and a distal end;
    a first electrode provided at said distal end and having an exposed electrode surface facing distally of said catheter main body, said first electrode being adapted to be electrically coupled to device for generating a current; and
    a second electrode disposed distally of said first electrode, said second electrode being adapted to be electrically coupled to said current generating device, said second electrode having an exposed surface in a plane substantially perpendicular to said longitudinal axis of said catheter main body;
    at least one of said first and second electrodes being movable relative to the other of said first and second electrodes so as to selectively capture a structure to be cauterized therebetween,
    wherein said first electrode is mounted to a distal end portion of said catheter main body, said distal end portion having a distal surface and a proximal surface, said distal surface being substantially perpendicular to said longitudinal axis and having said first electrode mounted thereon, said distal end portion having a diameter substantially greater than a diameter of a remainder of said catheter main body.

2. A bipolar electrocautery valvulotome as in claim 1, comprising an insulated guidewire structure extending axially from said second electrode and axially through the catheter main body, said second electrode being adapted to be electrically coupled to said device for generating a current via said insulated guide wire structure.

3. A bipolar electrocautery valvulotome as in claim 2, wherein said guide wire is sufficiently rigid to permit selectively displacement of said second electrode axially away from said first electrode by advancing said guide wire relative to said catheter main body.

4. A bipolar electrocautery valvulotome as in claim 1, wherein said proximal surface is at least one of inclined and curved so as to define a gradual transition in width from a side wall of said catheter main body to an outer periphery of said distal surface.

5. A bipolar electrocautery valvulotome as in claim 1, wherein said second electrode is substantially circular.

6. A bipolar electrocautery valvulotome as in claim 1, wherein said first electrode is substantially circular in plan view.

7. A bipolar electrocautery valvulotome as in claim 1, wherein said first electrode includes a linear electrode segment.

8. A bipolar electrocautery valvulotome as in claim 1, further comprising an insulating lip provided adjacent to at least one of said first and second electrodes.

9. A bipolar electrocautery valvulotome comprising:
    an elongated catheter main body having a longitudinal axis, a proximal end for being held and manipulated by a user, and a distal end;
    a first electrode provided at said distal end and having an exposed electrode surface facing distally of said catheter main body, said first electrode being adapted to be electrically coupled to device for generating a current;
    a second electrode disposed distally of said first electrode, said second electrode being adapted to be electrically coupled to said current generating device, said second electrode having an exposed surface in a plane substantially perpendicular to said longitudinal axis of said catheter main body;
    at least one of said first and second electrodes being movable relative to the other of said first and second electrodes so as to selectively capture a structure to be cauterized therebetween, and a head component having a distal end and a proximal end, said head component being at least one of inclined and curved so as to gradually increase in width from said distal end toward said proximal end, said proximal end including a surface disposed substantially perpendicular to said longitudinal axis of said catheter main body, said second electrode being mounted to said surface of said proximal end of said head component.

10. A bipolar electrocautery valvulotome as in claim 9, wherein said head component has a passage defined therethrough and a conduit in communication with said passage extends axially from said head component, through a lumen of said catheter main body.

11. A bipolar electrocautery valvulotome as in claim 10, wherein said passage extends axially through said head component from said proximal end to said distal end thereof.

12. A bipolar electrocautery valvulotome as in claim 9, further comprising an insulating lip provided adjacent to said second electrode.

13. A bipolar electrocautery valvulotome as in claim 12, wherein said insulating lip is provided in surrounding relation to said second electrode.

14. A bipolar electrocautery valvulotome as in claim 13, wherein said lip is formed from an insulating, biocompatible, resilient material.

15. A bipolar electrocautery valvulotome comprising:

an elongated catheter main body having a longitudinal axis, a proximal end for being held and manipulated by a user, and a distal end;

a first electrode provided at said distal end and having an exposed electrode surface facing distally of said catheter main body, said first electrode being adapted to be electrically coupled to device for generating a current; and a second electrode disposed distally of said first electrode, said second electrode being adapted to be electrically coupled to said current generating device, said second electrode having an exposed surface in a plane substantially perpendicular to said longitudinal axis of said catheter main body;

at least one of said first and second electrodes being movable relative to the other of said first and second electrodes so as to selectively capture a structure to be cauterized therebetween, wherein said first electrode comprises at least two electrode segments mounted to a distal portion of said catheter main body, said distal portion comprising at least two tab elements that can be selectively flexed relative to said longitudinal axis of said catheter main body, a said electrode segment being mounted to each said tab element.

16. A bipolar electrocautery valvulotome as in claim 15, wherein said tab elements can be flexed from a disposition that is inclined with respect to said longitudinal axis to a disposition that is substantially perpendicular to said longitudinal axis.

17. A method of disabling a venous valve using a valvulotome comprising an elongated catheter main body having a longitudinal axis, a proximal end for being held and manipulated by a user, and a distal end; a first electrode provided at said distal end and having an exposed surface facing distally of said catheter main body, said first electrode being electrically coupled to device for generating a current; a second electrode disposed distally of said first electrode, said second electrode being electrically coupled to said current generating device, said second electrode having an exposed surface facing proximally of said catheter main body and in a plane substantially perpendicular to said longitudinal axis of said catheter main body, at least one of said first and second electrodes being movable relative to the other of said first and second electrodes so as to selectively capture a structure to be cauterized therebetween, the method comprising the steps of:

a) making an incision in a target vein segment adjacent a first end of the vein segment;

b) inserting a distal end of said valvulotome through said incision with said first and second electrodes in opposed facing relation, c) advancing said valvulotome in a direction of blood flow through said vein segment to a second end of said vein segment;

d) displacing one of said first and second electrodes relative to the other so that said first and second electrodes are spaced apart;

e) passing said first electrode back through a valve in said vein segment;

f) displacing said second electrode to a position substantially immediately adjacent one side of said valve;

g) advancing said first electrode so as to sandwich said valve between said first and second electrodes; and h) actuating said current device whereby said valve is ablated.

18. A method as in claim 17, wherein steps d) through h) are repeated to sequentially ablate all valves of the vein segment from the second to the first end thereof.

* * * * *